United States Patent [19]

Ereren

[11] Patent Number: 5,318,586
[45] Date of Patent: Jun. 7, 1994

[54] LAPAROSCOPIC AND THORACOSCOPIC EXPANDABLE INSTRUMENTS

[76] Inventor: Erkan Ereren, 2554 N. Meridian Dr., Orange, Calif. 92667

[21] Appl. No.: 5,437

[22] Filed: Jan. 19, 1993

[51] Int. Cl.$^5$ .......................................... A61M 29/00
[52] U.S. Cl. .................................. 606/192; 128/20; 606/1; 606/198
[58] Field of Search ............... 606/192, 194, 195, 113, 606/114, 1; 604/104, 105, 106, 107, 108, 109; 128/20

[56] References Cited

U.S. PATENT DOCUMENTS

| | | | |
|---|---|---|---|
| 3,782,370 | 1/1974 | McDonald | 128/20 |
| 4,738,666 | 4/1988 | Fuqua | 606/108 |
| 5,190,555 | 3/1993 | Wetter et al. | 606/1 |
| 5,190,561 | 3/1993 | Graber | 606/114 |
| 5,195,507 | 3/1993 | Bilweis | 606/1 |

Primary Examiner—Tamara L. Graysay
Attorney, Agent, or Firm—G. Donald Weber, Jr.

[57] ABSTRACT

This invention relates to instruments such as retractors and dissectors used in laparoscopic and thoracoscopic surgical procedures. In particular, the invention relates to instruments with expandable portions thereof having different sizes and shapes which can be placed into the abdomen, chest or pelvis through small tubes and expanded using carbon dioxide or sterile solutions, for example. Expandable retractors will allow retracting of large, fragile organs such as the liver, spleen, kidney, lung, bowel while minimizing potential injuries thereto. Expandable dissectors which are used in dissecting arteries, veins and tubal structures are safer and more precise.

19 Claims, 2 Drawing Sheets

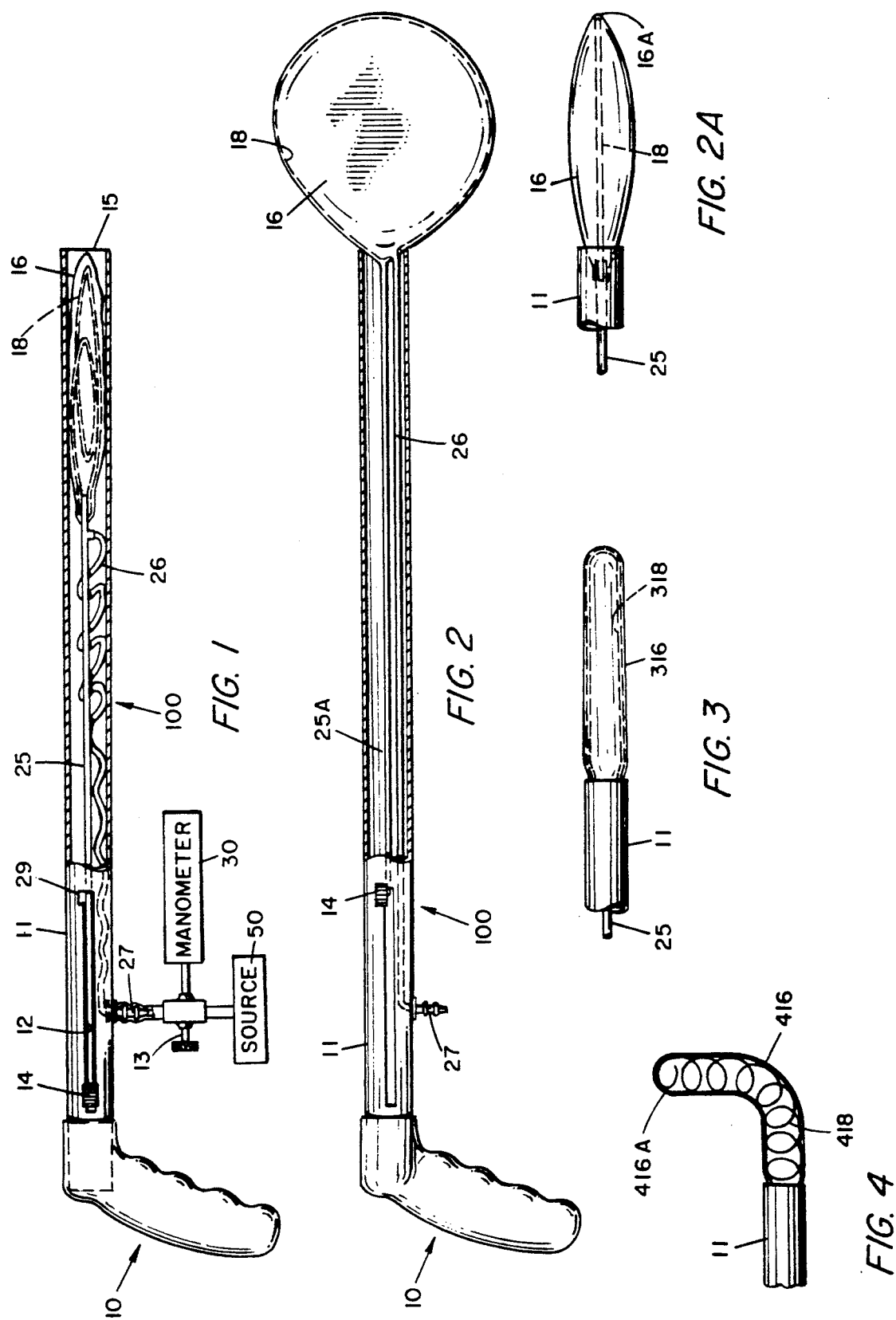

LAPAROSCOPIC AND THORACOSCOPIC EXPANDABLE INSTRUMENTS

BACKGROUND

1. Field of the Invention

This invention is directed to medical devices, in general, and to selectively expandable surgical instruments used in laparoscopic medical procedures, in particular.

2. Prior Art

There are many known medical tools, instruments and accessories now on the market. Many of these devices are used in conjunction with surgical procedures.

New types of surgical procedures are the laparoscopic and/or thorascoscopic procedures. These types of surgeries are relatively recent advances in abdominal, pelvic and/or chest surgeries wherein a surgical procedure in a body cavity is performed.

In laparoscopic procedures, unlike traditional surgery, there is no large incision made in the body. Rather, laparoscopic-types of surgeries are performed by placing small size tubes, for example, on the order of 5 mm, 10 mm and/or 12 mm diameter, through puncture-type openings of the abdominal, pelvic and/or chest cavities. The surgical instrument is then inserted through the tube (frequently referred to as a cannula) in order to perform the surgery within the body cavity.

Of course, other cannulas can be used for insertion of fiber optic light sources and/or cameras in order for the surgeon to view the interior of the cavity.

Many of the instruments utilized in the procedures include sharp portions which could, inadvertently, create an internal injury. Conversely, some of the instruments are relatively blunt and could produce trauma during the procedures.

In either event, it is highly desirable to permit the instruments to be as effective as possible during the procedures while causing as little unwanted trauma as possible. The currently available instruments are not very well adapted for these requirements.

PRIOR ART STATEMENT

During a preliminary patentability search, the following patents have been uncovered.

U.S. Pat. No. 3,774,596; COMPLIABLE CAVITY SPECULUM; G. B. Cook. This patent is directed to a device which includes collapsible walls which are folded during storage and during insertion and retraction from body cavity and expanded while therein.

U.S. Pat. No. 3,882,852; SURGICAL DILATORS HAVING INSUFFLATING MEANS: M. Sinnreich. This patent is directed to surgical instruments for obstetrical use including devices for dilating the certical neck and the uterus. It includes a pneumatically inflatable element.

U.S. Pat. No. 4,219,026; BLADDER HEMOSTATIC CATHETER; T. N. Layton. This patent is directed to a bladder hemostatic catheter which includes an inflatable balloon of elastic material covering a distal section of a shaft.

U.S. Pat. No. 4,291,687; INFLATABLE PACKING FOR SURGICAL USE HAVING AUXILIARY INTESTINAL SUPPORTING MEMBER; M. Sinnreich. This patent is directed to an inflatable, surgical packing material especially suited for filling the body cavity.

U.S. Pat. No. 4,299,227; OPTHALMOLOGICAL APPLIANCE; H.A. Lincoff. This patent is directed to a method of correcting retinal detachments wherein an expandable member is inserted into the eye through a small conjunctival incision.

U.S. Pat. No. 4,312,353; METHOD OF CREATING AND ENLARGING AN OPENING IN THE BRAIN; S. Shahbabian. This patent is directed to a method of creating and enlarging an opening in the brain using a catheter consisting of a stylette surrounded by an inflatable sac.

U.S. Pat. No. 4,501,264; MEDICAL SLEEVE; A.G. Rockey. This patent is directed to a method and article for medical diagnosis comprising a sleeve insertable in a natural body vessel to isolate material flowing into the vessel from direct contact with the interior surface of the vessel.

U.S. Pat. No. 4,651,717; MULTIPLE ENVELOPE TISSUE EXPANDER DEVICE: E.R. Jakubczak. This patent is directed to an implantable, multiple tissue expander which consists essentially of at least two inflatable envelopes and a method of using same.

U.S. Pat. No. 4,800,901; BALLOON-TYPE TISSUE EXPANSION DEVICE; L. Rosenberg. This patent is directed to a tissue expander device which has a main balloon portion for stretching tissue when implanted under the skin.

U.S. Pat. No. 5,007,898; BALLOON DILATION CATHETER; R. Rosenbluth et al. This patent is directed to an expandable dilation catheter and an axially elongated sheath, adapted for transurethral insertion.

SUMMARY OF THE INSTANT INVENTION

The instruments of this invention include a firm but flexible, tubular structure to which is attached an expandable tip. The tip can be designed to adopt various sizes and shapes. A support frame can be provided with the expandable tip in order to support the expanded tip when used for retracting, dissecting and similar purposes. An outer tube or sheath surrounds the tubular structure and the expandable tip in the retracted position. A handle or grip is provided at one end of the sheath. The handle is formed of rigid material and is designed to suit different purposes of the surgical procedures, for example, dissecting or retracting. A valve, for example a three way stop-cock, controls the injection of fluid or gas into the tubular structure to selectively expand the tip of the instrument.

BRIEF DESCRIPTION OF THE DRAWINGS

FIG. 1 is a schematic representation of one embodiment of the instant invention.

FIG. 2 is a representation of the device shown in FIG. 1 with the tip thereof in the expanded configuration.

FIG. 2A is a partial view of the instrument of FIG. 2 rotated 90°.

FIGS. 3 through 11 are variations of the design of the expandable tip of the instant invention.

DESCRIPTION OF A PREFERRED EMBODIMENT

Figure 5:
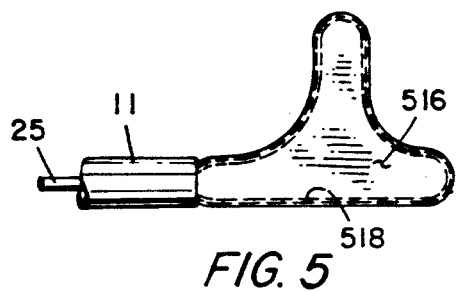

Referring now to FIG. 1, there is shown an instrument 100 fabricated in accordance with the instant invention. This instrument is specifically designed for laparoscopic and/or thoracoscopic surgical procedures. The instrument 100 includes a handle 10. The handle (or grip) can take any desired shape to enhance convenience of use of the instrument. In the embodiment shown in FIG. 1, a pistol-grip configuration is suggested.

Attached to the grip 10 is one end of an elongated, hollow sheath 11. The opposite end 15 of the tube 11 is open to the interior thereof. The sheath (or outer tube) 11 is relatively rigid to provide strength and rigidity to the instrument 100. The tube 11 is adapted to be inserted into the body cavity during the surgical procedures noted above.

A shaft or tube 25 is slidably mounted within the bore of hollow sheath 11. Tube 25, typically, is fabricated of a fairly strong, pliable material. In a preferred embodiment, tube 25 is hollow with an axial bore extending therealong.

The tube 11 includes slot 12 which extends through the sheath and axially along a portion thereof. The slot 12 is, typically, adjacent to the grip 10 end of the instrument 100. A suitable latch or tab 14 on the inner tube 25 and extends outwardly through slot 12 in tube 11. The tab 14 is slidably mounted within the slot 12 and is used to control the position of inner tube 25 relative to sheath 11. For example, when the tab 14 is in one position, for example in the leftmost position as shown in FIG. 1, the inner tube 25 is also at the leftmost position. Conversely, when the tab 14 is moved to the right (as shown in FIG. 2), the inner tube 25 is moved to the right. A detent 29 in the slot 12 is provided to retain tab 14 in the rightmost position (see FIG. 2) to maintain tube 25 in the extended position.

An expandable tip 16 is mounted to the end of the inner tube 25 by any suitable means, for example, by means of a non-toxic adhesive, sonic welding, threaded connector or any other suitable technique. The tip 16 moves in conjunction with inner tube 25. Thus, tip 16 is retained within outer tube 11 when tab 14 is in the leftmost position and extends out of tube 11 when tab 14 is in the rightmost position. The expandable tip 16 is a generally hollow, expandable, inflatable device similar to a balloon or the like. The expandable tip 16 is fabricated of a non-toxic, relatively strong, flexible and resilient material such as polypropylene or similar type of impervious material which is flaccid and deformable when not expanded. A spring-loaded collapsible frame 18 is provided within expandable tip 16. The frame 18 is also attached to the end of inner tube 25 in any conventional manner. Thus, frame 18 moves in conjunction with inner tube 25 expandable tip 16. The configuration of the frame 18 is, to at least some degree, determined by the desired shape of the expandable tip 16. The frame 18 is adapted to expand when the tube 25 and the tip 16 are pushed out of the end 15 of outer tube 11. The frame 18 provides additional stability and support to the flexible tip 16 when expanded. The frame 18 is not required in all embodiments. However, it is shown in FIG. 2 to illustrate the arrangement thereof.

Adjacent to the handle 10 (or grip) end of the instrument 100 is an inlet port 27, which is adapted to be connected to a source 50 of inflating material such as carbon dioxide ($CO_2$), sterile water, a saline solution or the like by means of a two-way or three-way valve 13 or the like. The valve 13 operates to control the flow of the inflating material (which can be a suitable compressed fluid) from source 50 into tube 25 and the expandable tip 16. Thus, in one position, the valve 13 is blocked so that the inflating material provided thereto is prevented from entering the instrument 100. When the valve 13 is moved to the open position, the inflating material can be inserted into the instrument, as described hereinafter.

If a three-way valve 13 is used, a manometer 30 (or similar device) can be used to measure and monitor the pressure of the inflating material in the tip 16.

A flexible conduit-tube 26 is connected between port 27 and the inner tube 25. The tube 26 carries the expansion material from valve 13 to the interior of tube 25 whereby the material is supplied to the expandable tip. Tube 26 is quite flexible so that it can travel along with inner tube 25 when retracted or extended.

Referring now to FIG. 2, there is shown instrument 100 which is substantially similar to the instrument 100 shown in FIG. 1. However, in the illustration of FIG. 2, the control tab 14 has been moved to the right (i.e. operational) position wherein the inner tube 25A and the attached expandable tip 16 are moved to the right. Thus, the expandable tip 16 extends outwardly from tube 11. The expanding material is then passed through valve 13 and port 2 into the interior of the expandable tip 16. Typically, the interior of the expandable tip 16 communicates with the axial bore in inner tube 25 (see FIG. 1). Thus, when the expanding material (e.g. $CO_2$ or sterile saline solution) is supplied to tube 25A via port 27 and flexible tube 26, the expandable tip 16 is caused to expand. As the tip 16 expands, it takes the prescribed shape (as described hereinafter) at the end of the tube 11. Alternatively, as shown in FIG. 2, flexible tube 26 can be connected directly to the expandable tip 16. In this case, tube 25A can be a solid rod, if desired.

As shown in FIG. 2, the expandable tip 16 has been moved outwardly from the "normal" resting place inside end 15 of tube 11. In this embodiment, the expanded tip 16 has a paddle-shaped configuration. The tip 16 is relatively thin cross-sectionally and is used to provide any kind of retraction and/or dissection operation during the surgical procedure.

Referring now to FIG. 2A, there is shown a partial view of the apparatus shown in FIGS. 1 and 2. In particular, FIG. 2A is an edge or top view of the end of the instrument 100 with the expandable tip 16 extended. In this embodiment, the edge view of the tip 16 is shown to have an elongated, slightly flattened configuration. Thus, the tip 16 can take a "clamshell" shape, if desired. The edge 16A or perimeter thereof is relatively narrow to provide a separating capability relative to the internal organs of the patient being operated on. However, the edge 16A of the tip 16 is not sufficiently sharp to cause trauma or injury to other organs. Alternatively, of course, the edge 16A can be relatively wide and flat, if desired.

Referring now to FIGS. 3 through 11, there are shown different configurations of the expandable tip. In particular, FIG. 3 shows an expandable tip 316 which is relatively straight and narrow, much in the nature of a knife blade or the like. A spring 318 may or may not be utilized to provide strength and rigidity, as desired.

FIG. 4 shows a "right angle" tip 416. The arm 416A can extend in either direction (relative to the grip 10), depending upon the utilization of the instrument. Thus, a "right angle" or a "left angle" tip 416 can be specified with regard to the grip 10 of the instrument. That is, when the instrument is held in the hands of the operator, a right hand or left hand angle is determined. Again, a suitable spring 418 may be utilized, as desired.

FIG. 5 is a combination tip 516 which includes a straight and an angled tip. Tip 516 combines the straight tip shown in FIG. 3 with an angled tip shown in FIG. 4. (Of course, the opposite direction angle can be achieved, as well.) The spring 518 can be utilized if so desired.

Figure 6:
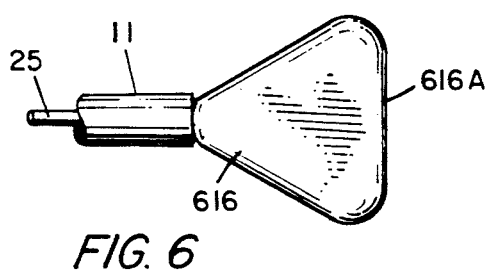

FIG. 6 shows a triangular tip 616 wherein the outer end 616A of the tip 616 is larger than the end thereof which is attached to the tube 25 of the instrument 100.

Figure 7:
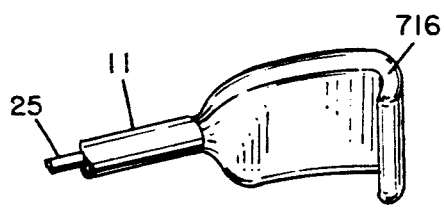

Referring now to FIG. 7, there is shown a curved tip 716 which is especially useful during retraction and/or exploration surgical procedures. It is noted that the curved tip 716 has a scoop-like configuration which permits the operator to grasp any internal organs in such a fashion as to gently and non-traumatically move same, if necessary.

Figure 8:
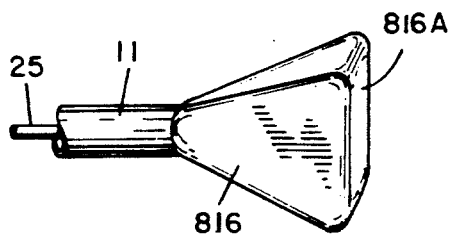

FIG. 8 shows tip 816 which is a variation of the triangular tip 616. Tip 816 is representative of a relatively thick (or wide) paddle-shaped tip. The edge 816A is relatively wide and flat to provide a blunt surface for positioning, moving or retaining internal body organs during a surgical procedure. Thus, a "wide" or slab-like configuration can be utilized in any of the tips shown and described herein.

Figure 9:
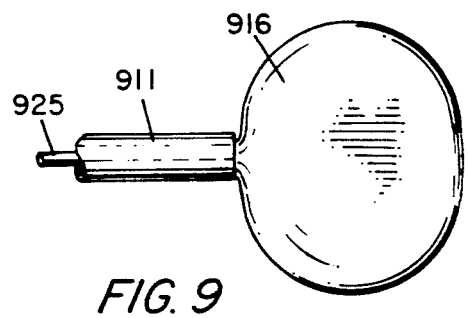

FIG. 9 shows tip 916 which is a variation of an elongated shape which could be a pair of angled tips, a pancake-shaped tip, or the like. Alternatively, tip 916 can take the shape of a sphere or a slightly oblate sphere.

Figure 10:
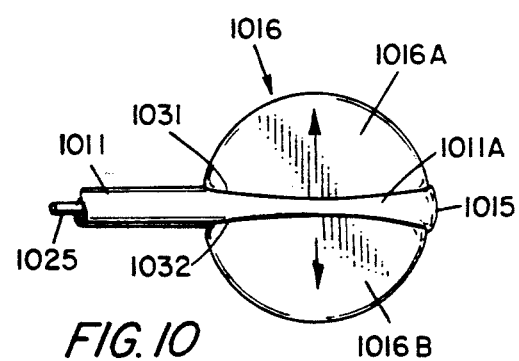

Referring now to FIG. 10, there is shown another embodiment of the instant invention. In this instance, the outer tube 1011 is closed at the end 1015 but incorporates a pair of openings 1031 and 1032 at diametrically opposed portions of the periphery of the tube. These openings are provided in lieu of the end opening in tube 1025. In this instance, a pair of inflatable tips 1016A and 1016B are provided. The pair of inflatable tips expand (or contract) through the pair of diametrically opposed openings in the tube 1011. Of course, a single inflatable tip can be attached to tube 1025 and expanded outwardly through the openings 1031 and 1032. In this fashion, a tip 1016 in the paddle configuration is formed. The end portion of tube 1011, including the thin sidewall portions 1011A, provides additional rigidity and strength to the tip.

Figure 11:
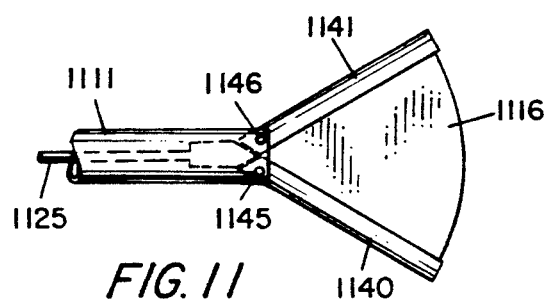

Referring now to FIG. 11, there is shown a modified version of the invention. In this case, a pair of jaw-like members 1140 and 1141 are pivotally mounted to the end of the shaft (i.e. rod or tube) 1125 (or, alternatively, to the end of tube 1111). The members (or jaws) are adhered to an expandable tip 1116 or balloon-like arrangement fabricated of materials similar to the expandable tips described above. In this instance, when the inflating material is supplied via tube 1125, the expandable tip 1116 expands and causes the jaws 1140 and 1141 to pivot about the respective pivot mountings 1145 and 1146. The jaws, in this case, tend to add rigidity and strength to the expandable tip 1116.

The jaws may be spring-loaded so that they will collapse when the inflating material is withdrawn from the tip via tube 1125. Of course, the jaws may merely pivot freely to the closed position (when the expanding materials are withdrawn) wherein the tip can be retracted into outer tube 1111.

Thus, there is shown and described a unique design and concept of instruments such as retractors and dissectors used in laparoscopic and thoracoscopic surgical procedures. The particular configuration shown and described herein relates to expandable instruments which can be inserted into a body cavity for retraction and dissection purposes. While this description is directed to a particular embodiment, it is understood that those skilled in the art may conceive modifications and/or variations to the specific embodiments shown and described herein. Any such modifications or variations which fall within the purview of this description are intended to be included therein as well. It is understood that the description herein is intended to be illustrative only and is not intended to be limitative. Rather, the scope of the invention described herein is limited only by the claims appended hereto.

I claim:

1. A medical instrument comprising,
   hollow tube means,
   handle means connected to one end of said hollow tube means,
   shaft means movably disposed within said hollow tube means,
   latch means interposed between said hollow tube means and said shaft means to selectively maintain the relative positions thereof,
   expandable means attached to said shaft means and movable therewith,
   said expandable means includes an impervious membrane arranged to have a pre-determined configuration when expanded, and
   expanding means connected to said expandable means and selectively operable to cause said expandable means to expand.

2. The instrument recited in claim 1 wherein,
   said shaft means is hollow.

3. The instrument recited in claim 1 wherein,
   said expanding means is connected to said expandable means via said shaft means.

4. The instrument recited in claim 1 wherein,
   said expanding means includes a source of expanding material which is supplied to said expandable means.

5. The instrument recited in claim 4 wherein,
   said expanding material comprises a compressed fluid.

6. The instrument recited in claim 1 wherein,
   said membrane is flaccid and deformable when not expanded.

7. The instrument recited in claim 1 including,
   frame means associated with said expandable means for determining the configuration of said expandable means when expanded.

8. The instrument recited in claim 7 wherein,
   said frame means comprises a spring-loaded component.

9. The instrument recited in claim 7 wherein,
   said frame means is disposed within said expandable means.

10. The instrument recited in claim 1 including,
    conduit means connecting said expanding means to said expandable means.

11. The instrument recited in claim 10 wherein,
    said shaft means is a rod.

12. The instrument recited in claim 1 including,
    valve means for controlling the operation of said expanding means.

13. The instrument recited in claim 1 including,
    pressure detector means connected to said expanding means for detecting the pressure applied to said expandable means.

14. The instrument recited in claim 1 wherein,
    said hollow tube means includes an axially extending slot through a portion of said hollow tube means,
    said slot includes a detent at least one end thereof, and said latch means includes tab means attached to said shaft means and extending through said slot in said hollow tube whereby said shaft means may be selectively moved and latched relative to said hollow tube by selectively engaging said tab means in said detent.

15. A medical instrument comprising, hollow tube means, handle means connected to one end of said hollow tube, shaft means movably disposed within said hollow tube an expandable means attached to one end of said shaft and movable therewith relative to said hollow tube, source means connected to said expandable means and selectively operable to supply an expansion medium which causes said expandable means to expand, a frame member disposed within said expandable means and adapted to assist in determining the configuration of said expandable means when expanded, latch means interposed between said hollow tube and said shaft to selectively maintain the relative positions thereof and prevent relative movement thereof, a valve connected between said source means and said expandable means for controlling the supply of said expansion medium to said expandable means, and pressure detector means connected to said valve means for detecting the pressure of the expansion medium applied to said expandable means.

16. The instrument recited in claim 15 wherein, said frame member comprises a collapsible spring.

17. The instrument recited in claim 15 wherein, said expandable means comprises an impervious membrane with smooth surfaces.

18. The instrument recited in claim 15 wherein, a port connected to said source means, and a conduit connected between said port and said expandable means for conducting said expansion medium therethrough.

19. The instrument recited in claim 16 wherein, said shaft is a hollow tube at least a portion of which is connected between said conduit and said expandable means for conducting said expansion medium therethrough.

* * * * *